US007358247B2

(12) United States Patent
Molnar et al.

(10) Patent No.: US 7,358,247 B2
(45) Date of Patent: Apr. 15, 2008

(54) MYCOPHENOLATE MOFETIL IMPURITY

(75) Inventors: Sandor Molnar, Debrecen (HU);
Tivadar Tamas, Debrecen (HU); Janos Hajko, Debrecen (HU); Beáta Kosztya, Debrecen (HU); Amihai Eisenstadt, Ramat-Hasharon (IL)

(73) Assignee: TEVA Gyógyszergyár Zártköruen Muködö Részvénytársaság, Debrecen (HU)

( * ) Notice: Subject to any disclaimer, the term of this patent is extended or adjusted under 35 U.S.C. 154(b) by 511 days.

(21) Appl. No.: 11/115,593

(22) Filed: Apr. 26, 2005

(65) Prior Publication Data

US 2005/0282806 A1    Dec. 22, 2005

Related U.S. Application Data

(60) Provisional application No. 60/566,056, filed on Apr. 27, 2004, provisional application No. 60/572,985, filed on May 20, 2004, provisional application No. 60/589,400, filed on Jul. 19, 2004, provisional application No. 60/638,478, filed on Dec. 23, 2004, provisional application No. 60/639,151, filed on Dec. 22, 2004, provisional application No. 60/642,867, filed on Jan. 10, 2005, provisional application No. 60/661,485, filed on Mar. 15, 2005.

(51) Int. Cl.
*C07D 413/14* (2006.01)
*A61K 31/5377* (2006.01)

(52) U.S. Cl. .................. 514/232.5; 544/106; 544/111; 514/231.2; 514/231.8; 514/232.2

(58) Field of Classification Search ................ 544/106, 544/111; 514/231.2, 231.8, 232.2, 232.5
See application file for complete search history.

(56) References Cited

U.S. PATENT DOCUMENTS

| | | | |
|---|---|---|---|
| 4,452,891 A | 6/1984 | Kida et al. |
| 4,748,173 A | 5/1988 | Nelson et al. |
| 4,753,935 A | 6/1988 | Nelson et al. |
| 4,786,637 A | 11/1988 | Allison et al. |
| 4,808,592 A | 2/1989 | Nelson et al. |
| 4,861,776 A | 8/1989 | Nelson et al. |
| 4,868,153 A | 9/1989 | Allison et al. |
| 4,948,793 A | 8/1990 | Allison et al. |
| 4,952,579 A | 8/1990 | Nelson et al. |
| 5,247,083 A | 9/1993 | Knox et al. |
| 5,455,045 A | 10/1995 | Samuels et al. |
| 5,543,408 A | 8/1996 | Fu et al. |
| 5,545,637 A | 8/1996 | Fu et al. |
| 5,688,529 A | 11/1997 | Lidgate et al. |
| 6,333,198 B1 | 12/2001 | Edmeades et al. |
| 6,709,846 B1 | 3/2004 | Sircar et al. |

2004/0167130 A1    8/2004    Lee et al.

FOREIGN PATENT DOCUMENTS

| | | |
|---|---|---|
| AU | 3619/71 | 5/1973 |
| EP | 0 281 713 | 9/1988 |
| EP | 0 963 980 | 12/1999 |
| GB | 1157099 | 7/1969 |
| GB | 1158387 | 7/1969 |
| WO | WO 94/01427 | 1/1994 |
| WO | WO 97/38689 | 10/1997 |
| WO | WO 00/34503 | 6/2000 |
| WO | WO 01/21607 | 3/2001 |
| WO | WO 01/64931 | 9/2001 |
| WO | WO 02/100855 | 12/2002 |
| WO | WO 2004/020426 | 3/2004 |
| WO | WO 2004/064806 | 8/2004 |
| WO | WO 2004/087174 A1 | 10/2004 |
| ZA | 68/4959 | 11/1967 |

OTHER PUBLICATIONS

Abraham, "The Effect Of Mycophenolic Acid On The Growth Of *Staphylococcus aureus* In Heart Broth", *Biochem. J.*, 1945, pp. 398-408, vol. 39, No. 5.
Ando, et al., "Antiviral Activity Of Mycophenolic Acid Studies On Antiviral And Antitumor Antibiotics. IV", *The Journal of Antibiotics*, Aug. 19, 1968, pp. 649-652, vol. 21, No. 11.
Bentley, "Bartolomeo Gosio, 1863-1944: An Appreciation", *Advances In Applied Microbiology*, 2001, pp. 229-251, vol. 48.
Bentley, "Mycophenolic Acid: A One Hundred Year Odyssey From Antibiotic To Immunosuppressant", *Chem. Rev.* 2000, pp. 3801-3825, vol. 100, No. 10.
Guillory, "Polymorphism in Pharmaceutical Solids", *Drugs and the Pharmaceutical Sciences*, edited by BRITTAIN, 1999, pp. 184-222, vol. 95, Marcel Dekker, Inc.
Clutterbuck, et al., "The Metabolic Products Of The Penicillium Brevi-Compactum Series", *Studies In The Biochemistry Of Micro-Organisms*, 1932, pp. 1441-1458.
Craig, et al., "The Relevance Of The Amorphous State To Pharmaceutical Dosage Forms: Glassy Drugs And Freeze Dried Systems", *International Journal of Pharmaceutics*, 1999, pp. 179-207, vol. 179.
Desrosiers, et al., "High Throughput Screening Techniques For Pre-Formulation: Salt Selection And Polymorph Studies", *Acta Cryst.*, 2002, A58 (Supplement), C9.
Filtenborg, et al., "Simple Screening Method For Molds Producing Intracellular Mycotoxins In Pure Cultures", *Applied and Environmental Microbiology*, Feb. 1983, pp. 581-585, vol. 45, No. 2.
Franklin, et al., "The Inhibitin Of Nucleic Acid Synthesis By Mycophenolic Acid", *Biochem. J.*, 1969, pp. 515-524, vol. 113.

(Continued)

*Primary Examiner*—Golam M. M. Shameem
(74) *Attorney, Agent, or Firm*—Kenyon & Kenyon LLP (57) ABSTRACT

Provided is an impurity of mycophenolate mofetil, processes for its preparation and its use as a reference.

20 Claims, 5 Drawing Sheets

OTHER PUBLICATIONS

Frisvad, et al., "Classification Of *Terverticillate penicillia* Based On Profiles Of Mycotoxins And Other Secondary Metabolites", *Applied and Environmental Microbiology*, 1983, pp. 1301-1310, vol. 46, No. 6.

Gainer, et al., "GLC Of Mycophenolic Acid And Related Compounds", *Journal of Pharmaceutical Sciences*, 1970, pp. 1157-1159, vol. 59, No. 8.

Gilliver, "The Inhibitory Action Of Antibiotics On Plant Pathogenic Bacteria And Fungi", *Annals of Botany, N.S.*, 1946, pp. 271-282, vol. 10, No. 39.

Gosio, "Sur La Reconnaissance De L'Arsenic, Au Moyen De Certaines Moisissures", *Archives Italiennes De Biologie*, 1893, pp. 299-305.

Gu, et al., "Grouping Solvents By Statistical Analysis Of Solvent Property Parameters: Implication To Polymorph Screening", *International Journal of Pharmaceutics*, 2004, pp. 117-125, vol. 283.

Gu, et al., "Polymorph Screening: Influence Of Solvents On The Rate Of Solvent-Mediated Polymorphic Transformation", *Journal of Pharmaceutical Sciences*, 2001, pp. 1878-1890, vol. 90, No. 11.

Hilfiker, et al., "Polymorphism—Integrated Approach From High-Throughput Screening To Crystallization Optimization", *Journal of Thermal Analysis and Calorimetry*, 2003, pp. 429-440, vol. 73.

Makara, et al., "Nuclear Magnetic Resonance And Molecular Modeling Study On Mycophenolic Acid: Implications For Binding To Monophosphate Dehydrogenase", *Journal of Medicinal Chemistry*, 1996, pp. 1236-1242, vol. 39, No. 6.

Noto, et al., "Some Biological Properties Of Mycophenolic Acid", *The Journal of Antibiotics*, 1969, pp. 165-169, vol. 22, No. 4.

Nowak, et al., "Mycophenolic Acid Binding To Human Serum Albumin: Characterization And Relation To Pharmodynamics", *Clinical Chemistry*, 1995, pp. 1011-1017, vol. 41, No. 7.

Rihs, et al., "Sodium Mycophenolate", *Acta Crystallographica*, 2000, pp. 432-433, vol. C56.

Snyder, et al., *Introduction To Modern Liquid Chromatography*, $2^{nd}$ Ed., 1979, pp. 549-572, John Wiley & Sons, Inc.

Sollinger, Hans W., "Mycophenolate Mofetil", *Kidney International*, 1995, pp. S-14-S-17, vol. 48, Suppl. 52.

Strobel, et al., *Chemical Instrumentaiton: A Systematic Approach*, $3^{rd}$ Ed., 1989, pp. 391-393, 879-894, 922-925, 953.

Wagner, et al., "Carboxylic Esters", *Synthetic Organic Chemistry*, 1953, pp. 479-531.

Wiwattanawongsa, et al., "Determination Of Mycophenolic Acid And Its Phenol Glucuronide Metabolite In Human Plasma And Urine By High-Performance Liquid Chromatography", *Journal of Chromatography B*, 2001, pp. 35-45, vol. 763.

Rihs et al., "Metal-Organic Compounds: Sodium Mycophenolate", *Acta Crystallographic* 2000, C56, pp. 423-433.

Wrigglesworth et al. "Analogues of Capsaicin with Agonist Activity as Novel Analgesic Agents: Structure-Activity Studies", *Journal of Medicinal Chemistry*, 1996, pp. 4942-4951, vol. 39, No. 25.

Caira, "Crystalline Polymorphism of Organic Compounds", *Topics In Current Chemistry*, 1998, pp. 163-208. vol. 198.

Sadhukhan et al. "Optimization of Mycophenolic Acid Production in Solid State Fermentation Using Response Surface Methodology", *Journal of Industrial Microbiology and Biotechnology*, 1999, pp. 33-38, vol. 22, No. 1.

Makara et al. "Nuclear Magnetic Resonance and Molecular Modeling Study on Mcyophenolic Acid: Implications for Binding to Inosine Monophosphate Dehydrogenase", *Journal of Medicinal Chemistry*, 1996, pp. 1236-1242, vol. 39, No. 6+.

¹H chemical shifts

| ¹H - ppm | Hydrogen | $CH_n$ |
|---|---|---|
| 1.73 (s) | 4'-$CH_3$ | $CH_3$ |
| 2.10 (s) | 7-$CH_3$ | $CH_3$ |
| 2.21 (t) | 3' | $CH_2$ |
| 2.32 (t) | 2' | $CH_2$ |
| 2.39 (m) | 3" | 2*$CH_2$ |
| 2.49 (m) | 3''' | 2*$CH_2$ |
| 2.49 (m) | 2''' | 2*$CH_2$ |
| 2.74 (t) | 2" | $CH_2$ |
| 3.38 (d) | 6' | $CH_2$ |
| 3.60 (t) | 4" | 2*$CH_2$ |
| 3.64 (t) | 4''' | 2*$CH_2$ |
| 3.69 (s) | 6-$OCH_3$ | $CH_3$ |
| 4.08 (t) | 1" | $CH_2$ |
| 4.26 (t) | 1''' | $CH_2$ |
| 5.05 (s) | 1 | $CH_2$ |
| 5.09 (t) | 5' | CH |

$^{13}C$ chemical shifts

| $^{13}C$ -ppm | Carbon | $CH_n$ |
|---|---|---|
| 11.35 | 7-$CH_3$ | $CH_3$ |
| 16.15 | 4'-$CH_3$ | $CH_3$ |
| 23.33 | 6' | $CH_2$ |
| 32.78 | 2' | $CH_2$ |
| 34.27 | 3' | $CH_2$ |
| 53.60 | 3" | $CH_2$ |
| 53.70 | 3'" | $CH_2$ |
| 56.88 | 2" | $CH_2$ |
| 58.38 | 2'" | $CH_2$ |
| 60.75 | 6-$OCH_3$ | $CH_3$ |
| 61.21 | 1" | $CH_2$ |
| 66.66 | 4" | $CH_2$ |
| 66.68 | 4'" | $CH_2$ |
| 68.11 | 1 | $CH_2$ |
| 71.91 | 1'" | $CH_2$ |
| 112.41 | 5 | C |
| 119.89 | 7 | C |
| 123.57 | 5' | CH |
| 128.90 | 3a | C |
| 133.51 | 4' | C |
| 146.55 | 7a | C |
| 155.32 | 4 | C |
| 162.68 | 6 | C |
| 168.78 | 3 | C |
| 172.89 | 1' | C |

Fig. 3

Experimental Conditions

Instrument: Bruker BioTof II mass spectrometer
Ionization mode: Electrospray in positive mode
Resolution: 5000
Sample concentration: $10^{-3}$ M in MeOH
Sample insertion: Cole Parmer 749000 syringe pump, Hamilton Microliter #810 syringe (2 µL/min)

Results and Discussion

According to the positive electrospray mass spectra the nominal molecular weight of the sample is 546.

| Peak Report | | | |
|---|---|---|---|
| Assignation | $M_{monois.\ calc.}$ (Da) | $M_{measured}$ (Da) | |
| [M+H]$^+$ | 547.30 | 547.29 | |
| [M+Na]$^+$ | 569.28 | 569.27 | |
| [M+K]$^+$ | 585.26 | 585.25 | |
| [2M+Na]$^+$ | 1115.58 | 1115.61 | |

The measured monoisotopic masses and isotopic distributions are in good agreement with those calculated based on the composition proposed ($C_{29}H_{42}N_2O_9$).

MYCOPHENOLATE MOFETIL IMPURITY

CROSS-REFERENCE TO RELATED APPLICATIONS

This application claims the benefits of U.S. Provisional Patent Application Nos. 60/566,056 filed Apr. 27, 2004, 60/572,985 filed May 20, 2004, 60/589,400 filed Jul. 19, 2004, 60/638,478 filed Dec. 23, 2004, 60/639,151 filed Dec. 22, 2004, 60/642,867 filed Jan. 10, 2005, 60/661,485 filed Mar. 15, 2005, the contents of all of which are incorporated herein by reference.

FIELD OF THE INVENTION

This invention relates to 2-(4-morpholinyl)ethyl (E)-6-(1,3-dihydro-4-[2-(4-morpholinyl)ethoxy]-6-methoxy-7-methyl-3-oxo-isobenzofuran-5-yl)-4-methyl-hex-4-enoate (Compound 1), an impurity of mycophenolate mofetil, a process for preparing and isolating thereof, as well as its use as reference marker. The invention further relates to mycophenolate mofetil having a low amount of Compound 1, as well as the HPLC method for identifying thereof.

BACKGROUND OF THE INVENTION

Mycophenolic acid has the chemical name 6-[4-Hydroxy-6-methoxy-7-methyl-3-oxo-5-phthalanyl]-4-methyl-hex-4-enoic acid, 6-[1,3-Dihydro-4-hydroxy-6-methoxy-7-methyl-3-oxo-isobenzofuran-5-yl]-4-methyl-hex-4-enoic acid, molecular formula of $C_{17}H_{20}O_6$, molecular weight of 320.35, CAS Registry number of 24280-93-1 and a structure of:

Mycophenolic acid (MPA), isolated by Gosio in 1893, is the first well-characterized antibiotic (Bentley 2001). It is produced by several species of *Penicillium*, including *P. brevicompactum*, *P. scabrum*, *P. nagem*, *P. roqueforti*, *P. patrismei*, and *P. viridicatum* (Clutterbuck et al. 1932, Jens and Filtenborg 1983).

MPA, in addition to its antibiotic activity (Abraham 1945), also has antifungal (Gilliver 1946), antiviral (Ando et al. 1968), and antitumor properties (Noto et al. 1969), and has been used clinically in the treatment of psoriasis (Johnson 1972). More recently, it has been recognized as a powerful immunosuppressant (Bentley 2000).

At least one reason for its pharmacological properties is the fact that in several biological systems it interferes with guanine biosynthesis at the level of inosine monophosphate dehydrogenase (IMPD). It has, therefore, a pronounced inhibitory effect on nucleic acid synthesis (Franklin and Cook 1969). The inhibition of IMPD is also the basis of its lymphocyte-specific immunosuppressive effect. Since lymphocytes primarily depend on de novo guanine biosynthesis, the reduction of this pathway results in suppression of T and B lymphocyte proliferation.

MPA was withdrawn due to its high incidence of side effects (primarily infections such as herpes zoster and gastrointestinal side effects such as stomach discomfort). The 2-morpholinoethyl ester derivative, mycophenolate mofetil (CellCept®) does not have these drawbacks, and has a better bioavailability than mycophenolic acid. Mycophenolate mofetil was recently approved (in the United States in 1995 and in Europe in 1996) for prophylaxis of organ rejection in patients receiving allogeneic renal transplants (Shaw and Nowak 1995, Sollinger 1995). After oral administration the ester form rapidly hydrolyzes to free acid. MPA is then converted mainly to an inactive glucuronide metabolite, which is eliminated by urinary excretion (Bentley 2001, Wiwattanawongsa et al. 2001).

Chemically, mycophenolate mofetil (abbreviated as MMF) is 2-(4-morpholinyl)ethyl (E)-6-(1,3-dihydro-4-hydroxy-6-methoxy-7-methyl-3-oxo-isobenzofuran-5-yl)-4-methyl-4-hexenoate, and its first synthesis was disclosed in U.S. Pat. No. 4,753,935.

Mycophenolate mofetil

Another patent, U.S. Pat. No. 5,543,408 discloses the anhydrous crystalline salt form, monohydrate salt form, and amorphous salt form of mycophenolate mofetil. These forms are characterized by their melting points and/or Differential Scanning Calorimetric (DSC) results and/or powder X-ray diffraction pattern.

The product mixture of a reaction rarely is a single compound pure enough to comply with pharmaceutical standards. Side products and byproducts of the reaction and adjunct reagents used in the reaction will, in most cases, be present. At certain stages during processing of the mycophenolate mofetil contained in the product mixture into an active pharmaceutical ingredient ("API"), the mycophenolate mofetil must be analyzed for purity, typically by HPLC or GC analysis, to determine if it is suitable for continued processing or ultimately for use in a pharmaceutical product. The mycophenolate mofetil does not need to be absolutely pure. Absolute purity is a theoretical ideal that is unattainable. Rather, there are purity standards intended to ensure that an API is not made less safe for clinical use because of the presence of impurities.

The U.S. Food and Drug Administration's Center for Drug Evaluation and Research (CDER) has promulgated guidelines recommending that drug applicants identify organic impurities of 0.1% or greater in the active ingredient. "Guideline on Impurities in New Drug Substances," 61 Fed. Reg. 371 (1996); "Guidance for Industry ANDAs: Impurities in Drug Substances," 64 Fed. Reg. 67917 (1999). Unless an impurity has been tested for safety, is in a composition proven to be safe in clinical trials, or is a human metabolite, the CDER further recommends that the drug applicant reduce the amount of the impurity in the active ingredient to below 0.1%. Therefore, in order to study the pharmacology and toxicology of such impurities, there is a need to isolate impurities in drug substances.

In order to obtain marketing approval for a new drug product, manufacturers must submit to the regulatory authority evidence that the product is acceptable for administration to humans. Such a submission must include, among other things, analytical data showing the impurity profile of the product to demonstrate that the impurities are either absent, or present in a negligible amount. Therefore, there is a need for analytical methods to detect impurities, and for reference standards to identify and assay those impurities.

Generally, impurities (side products, byproducts, and adjunct reagents) are identified spectroscopically and by other physical methods and then the impurities are associated with a peak position in a chromatogram (or a spot on a TLC plate). (Strobel p. 953) (Strobel, H. A.; Heineman, W. R., *Chemical Instrumentation: A Systematic Approach*, 3rd dd. (Wiley & Sons: New York 1989)). Thereafter, the impurity can be identified by its position in the chromatogram, which is conventionally measured in minutes between injection of the sample on the column and elution of the particular component through the detector, known as the "retention time." This time period varies daily based upon the condition of the instrumentation and many other factors. To mitigate the effect that such variations have upon accurate identification of an impurity, practitioners use "relative retention time" ("RRT") to identify impurities. (Strobel p. 922). The RRT of an impurity is its retention time divided by the retention time of some reference marker. In theory, mycophenolate mofetil itself could be used as the reference marker, but as a practical matter it is present in such overwhelming proportion in the mixture that it tends to saturate the column, leading to irreproducible retention times, i.e., the maximum of the peak corresponding to mycophenolate mofetil tends to wander (Strobel FIG. 24.8 (b) p. 879, contains an illustration of the sort of asymmetric peak that is observed when a column is overloaded). Thus, it is sometimes desirable to select an alternative compound that is added to, or is present in, the mixture in an amount significant enough to be detectable and sufficiently low as not to saturate the column and to use that compound as the reference marker.

Researchers and developers in drug manufacturing understand that a compound in a relatively pure state can be used as a "reference standard" (a "reference marker" is similar to a reference standard but it is used for qualitative analysis) to quantify the amount of the compound in an unknown mixture. When the compound is used as an "external standard," a solution of a known concentration of the compound is analyzed by the same technique as the unknown mixture. (Strobel p. 924, Snyder p. 549) (Snyder, L. R.; Kirkland, J. J. *Introduction to Modern Liquid Chromatography*, 2nd ed. (John Wiley & Sons: New York 1979)). The amount of the compound in the mixture can be determined by comparing the magnitude of the detector response. See also U.S. Pat. No. 6,333,198, incorporated herein by reference.

The reference standard compound also can be used to quantify the amount of another compound in the mixture if the "response factor," which compensates for differences in the sensitivity of the detector to the two compounds, has been predetermined. (Strobel p. 894). For this purpose, the reference standard compound may be added directly to the mixture, in which case it is called an "internal standard." (Strobel p. 925, Snyder p. 552).

The reference standard compound can even be used as an internal standard when the unknown mixture contains some of the reference standard compound by using a technique called "standard addition," wherein at least two samples are prepared by adding known and differing amounts of the internal standard. (Strobel pp. 391-393, Snyder pp. 571, 572). The proportion of detector response due to the reference standard compound that is originally in the mixture can be determined by extrapolation of a plot of detector response versus the amount of the reference standard compound that was added to each of the samples to zero. (e.g. Strobel, FIG. 11.4 p. 392).

Esterification of MPA is known. (e.g. in *Synthetic Organic Chemistry* by R. B. Wagner and H. D. Zook, Wiley, New York, 1956, see pages 479-532). U.S. Pat. No. 4,753,935 first disclosed mycophenolate mofetil. However, the synthetic process to prepare the ester results in various impurities.

PHARMAEUROPA vol 15 No 4 October 2003 published a list of possible impurities of Mycophenolate Mofetil (from A to H). The present invention relates to a new impurity whose presence was observed in Mycophenolate Mofetil and which is not included in this list. This impurity is useful as a reference standard in preparation of highly pure mycophenolate mofetil.

SUMMARY OF THE INVENTION

In one aspect, the invention encompasses an 4-O-alkylated impurity of mycophenolate mofetil 2-(4-morpholinyl)ethyl (E)-6-(1,3-dihydro-4-[2-(4-morpholinyl)ethoxy]-6-methoxy-7-methyl-3-oxo-isobenzofuran-5-yl)-4-methyl-hex-4-enoate, denominated Compound 1, having the following chemical structure:

Compound 1

Compound 1 has the following $^1$H NMR (300 MHz, CDCl$_3$) δ (ppm): 1.73, 2.10, 2.21, 2.32, 2.39, 2.49, 2.74, 3.38, 3.60, 3.64, 3.69, 4.08, 4.26, 5.05, 5.09; $^{13}$C NMR (75 MHz, CDCl$_3$) δ (ppm): 11.35, 16.15, 23.33, 32.78, 34.27, 53.60, 53.70, 56.88, 58.38, 60.75, 61.21, 66.66, 66.68, 68.11, 71.91, 112.41, 119.89, 123.57, 128.90, 133.51, 146.55, 155.32, 162.68, 168.78, 172.89; and MS (Da): [M+H]$^+$547.29, [M+Na]$^+$569.27, [M+K]$^+$585.25, [2M+Na]$^+$ 1115.61

In another aspect, the invention is directed to a process for synthesizing Compound 1 by reaction of mycophenolate mofetil with an N-ethylmorpholine derivative.

Compound 1 may also be obtained by isolation from a sample of mycophenolate mofetil containing Compound 1 by a) providing a solution of mycophenolate mofetil in a suitable solvent; b) washing the mycophenolate mofetil solution with an aqueous acidic solution to obtain a two-phase system; c) separating the organic phase containing mycophenolate mofetil from the aqueous acidic phase; d) adding an aqueous basic solution to the aqueous acidic phase; and (e) recovering Compound 1.

The invention also provides a method for determining the purity of mycophenolate mofetil comprising comparing the purity of mycophenolate mofetil with Compound 1 as a reference standard, particularly a reference marker.

In another aspect, the present invention provides for mycophenolate mofetil having about 0.01 to about 0.1% of Compound 1% area by HPLC. Also provided is a pharmaceutical dosage form comprising said mycophenolate mofetil, and methods of treatment of a human who are at a risk of organ transplant rejection comprising administering the pharmaceutical composition to the human in need thereof.

In yet another aspect, the present invention provides an HPLC method for the analysis and assay of mycophenolate mofetil.

DETAILED DESCRIPTION OF THE INVENTION

Figure 1:
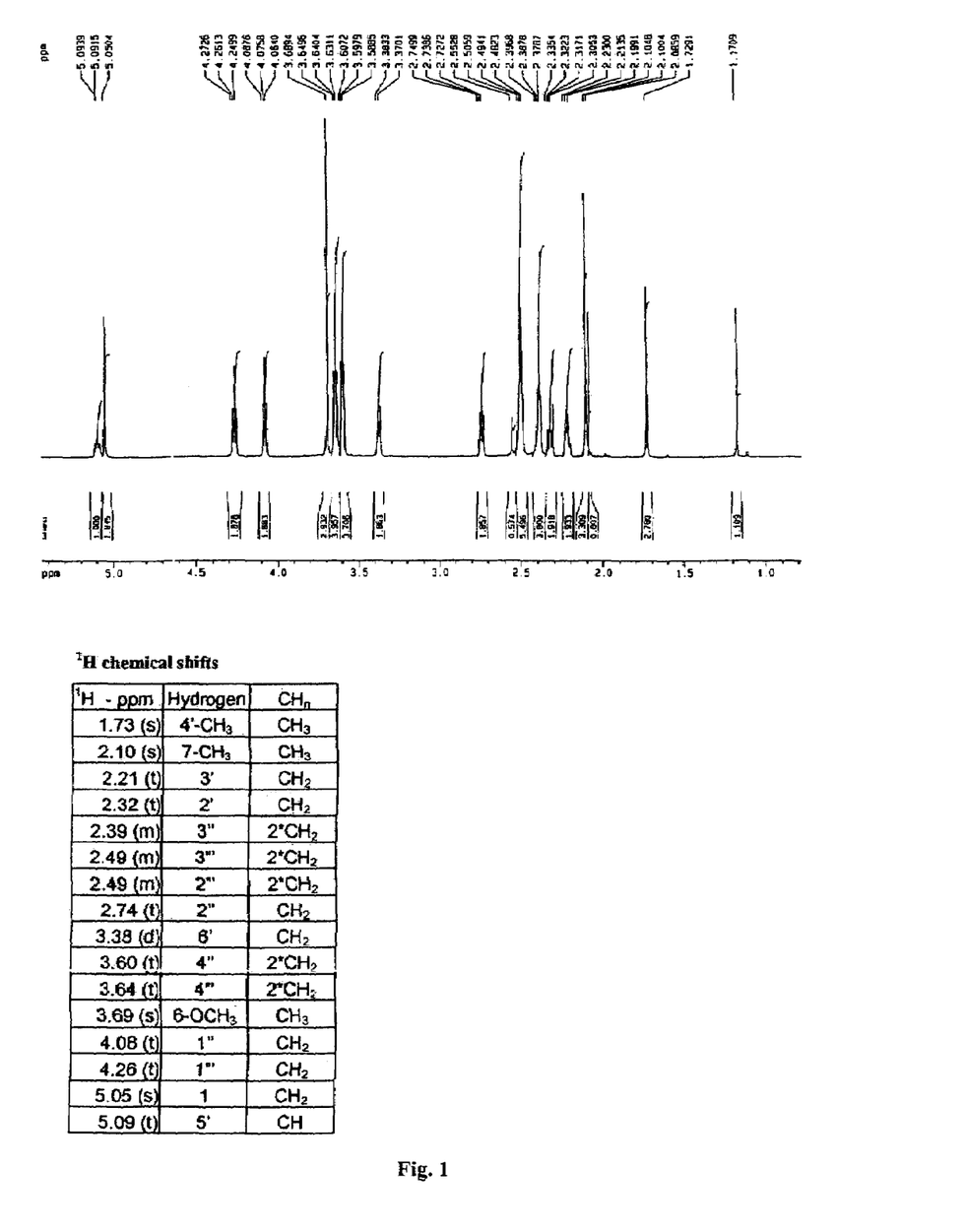
FIG. 1 is a representative $^1$H NMR spectrum for Compound 1.
Figure 2:
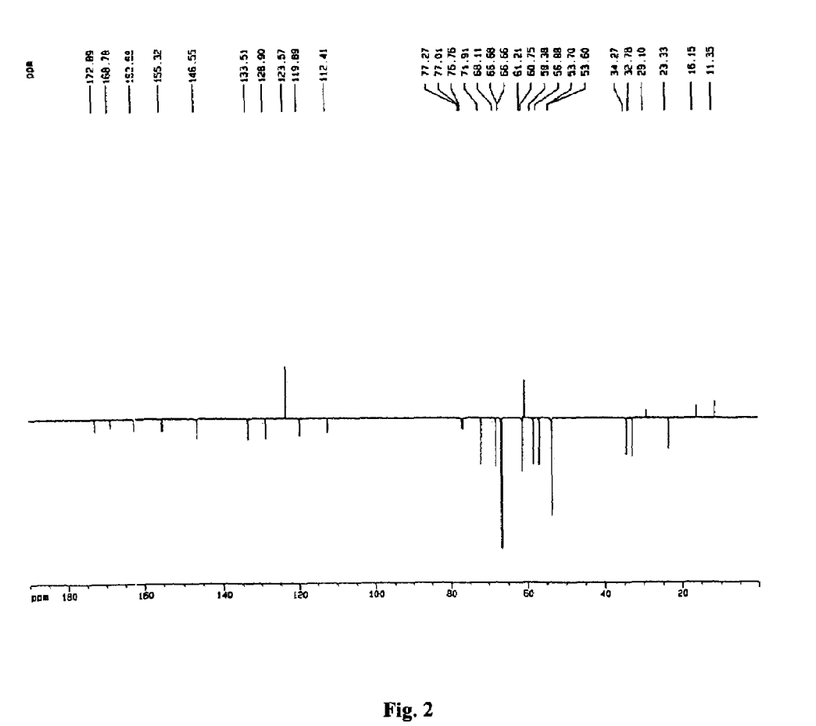
FIG. 2 is a representative for $^{13}$C NMR spectrum for Compound 1.
Figure 3:
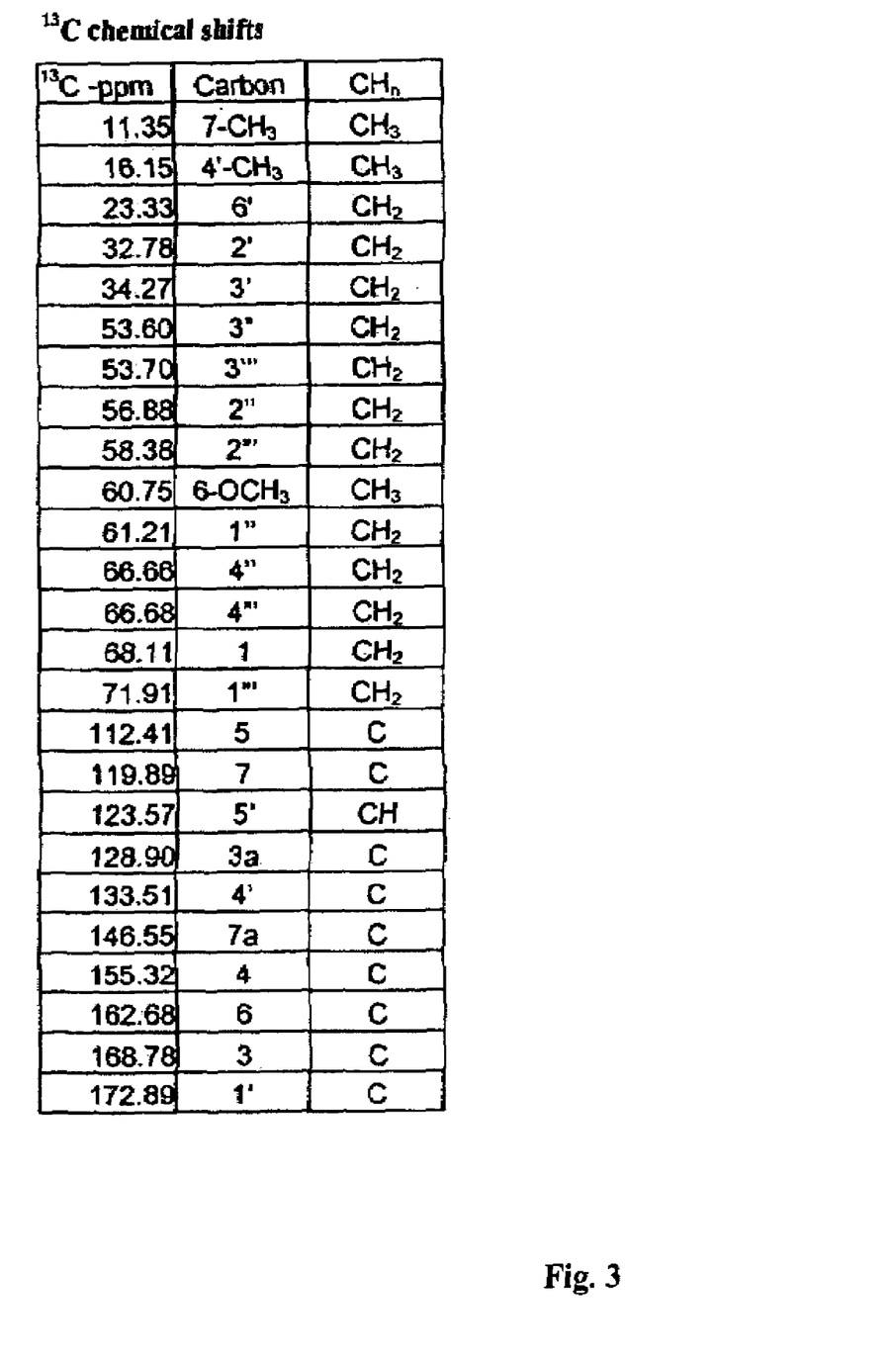
FIG. 3 is a representative $^{13}$C NMR spectral data for Compound 1.
Figure 4:
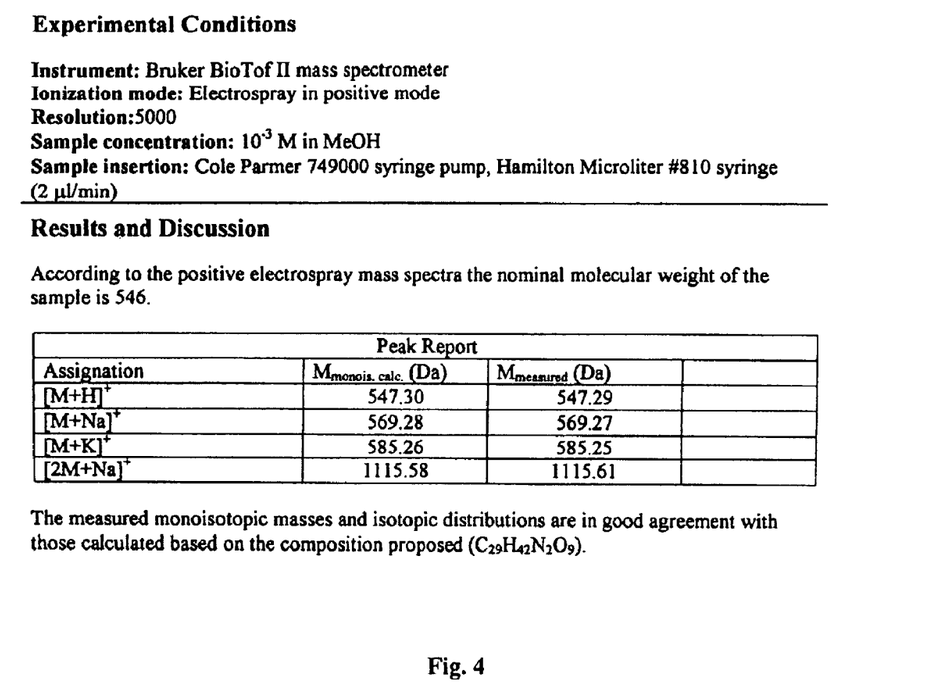
FIG. 4 is a representative MS data for Compound 1.
Figure 5:
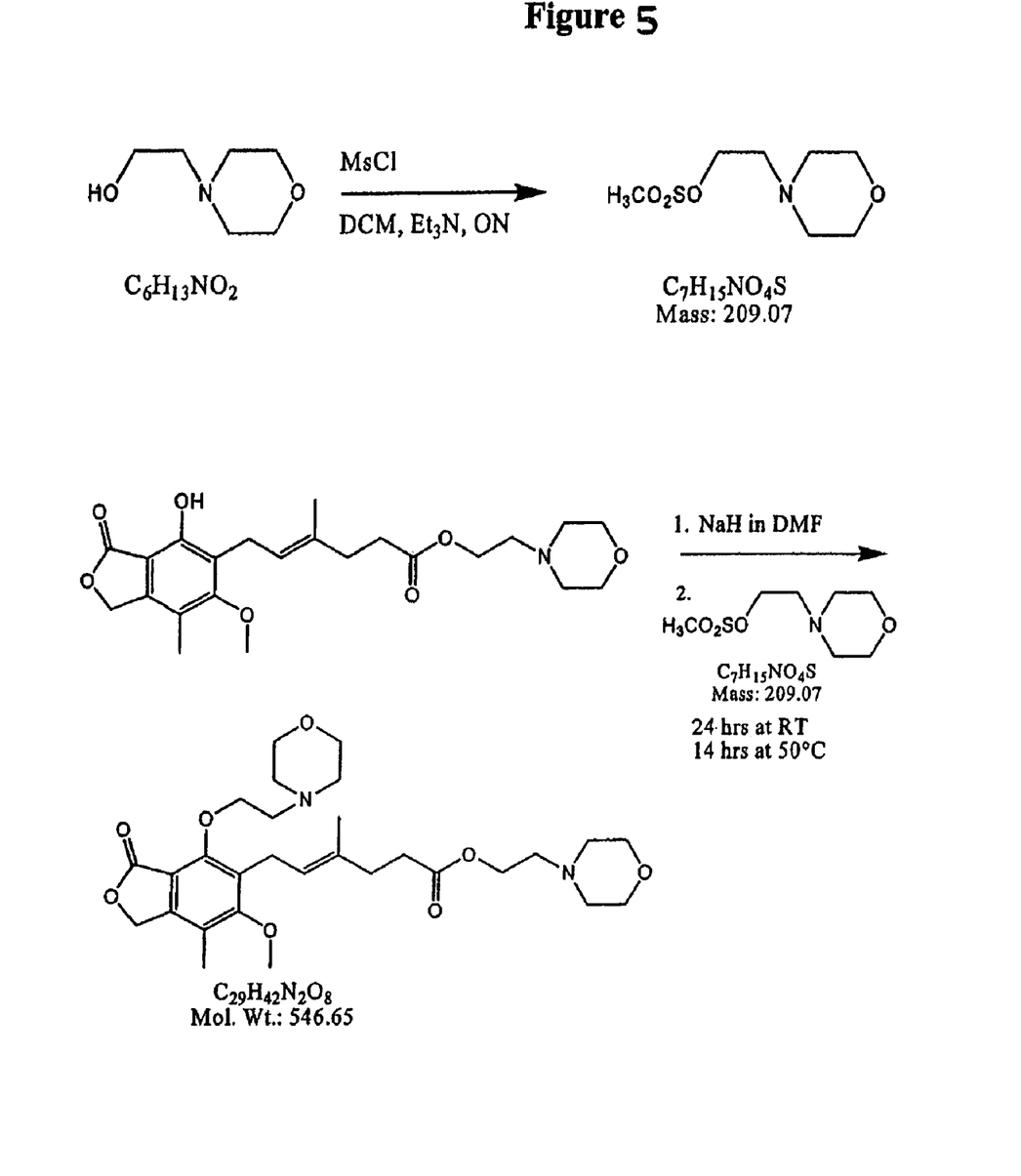
FIG. 5 depicts a process for the synthesis Compound 1.

As used herein, the term "reference standard" refers to a compound that may be used both for quantitative and qualitative analysis of an active pharmaceutical ingredient. For example, the retention time of the compound in HPLC allows for setting a relative retention time, thus making qualitative analysis possible. The concentration of the compound in solution before injection into an HPLC column allows for comparison of the areas under the peaks in an HPLC chromatogram, thus making quantitative analysis possible.

A "reference marker" is used in qualitative analysis to identify components of a mixture based upon their position, e.g. in a chromatogram or on a Thin Layer Chromatography (TLC) plate (Strobel pp. 921, 922, 953). For this purpose, the compound does not necessarily have to be added to the mixture if it is present in the mixture. A "reference marker" is used only for qualitative analysis, while a reference standard may be used for quantitative or qualitative analysis, or both. Hence, a reference marker is a subset of a reference standard, and is included within the definition of a reference standard.

Although some of the knowledge of those in the art regarding reference standards has been described in general terms up to this point, those skilled in the art also understand that the detector response can be, for example, the peak heights or integrated peak areas of a chromatogram obtained, e.g. by UV or refractive index detection, from the eluent of an HPLC system or, e.g. flame ionization detection or thermal conductivity detection, from the eluent of a gas chromatograph, or other detector response, e.g. the UV absorbence, of spots on a fluorescent TLC plate. The position of the reference standard may be used to calculate the relative retention time for mycophenolate mofetil and other impurities.

The present invention provides an impurity of mycophenolate mofetil (MMF), designated Compound 1. This impurity is useful as a reference standard, more particularly a reference marker.

Compound 1, or 2-(4-morpholinyl)ethyl (E)-6-(1,3-dihydro-4-[2-(4-morpholinyl)ethoxy]-6-methoxy-7-methyl-3-oxo-isobenzofuran-5-yl)-4-methyl-hex-4-enoate, has the following chemical structure:

Compound 1

Compound 1 has the following $^1$H NMR (300 MHz, CDCl$_3$) δ (ppm): 1.73, 2.10, 2.21, 2.32, 2.39, 2.49, 2.74, 3.38, 3.60, 3.64, 3.69, 4.08, 4.26, 5.05, 5.09; $^{13}$C NMR (75 MHz, CDCl$_3$) δ (ppm): 11.35, 16.15, 23.33, 32.78, 34.27, 53.60, 53.70, 56.88, 58.38, 60.75, 61.21, 66.66, 66.68, 68.11, 71.91, 112.41, 119.89, 123.57, 128.90, 133.51, 146.55, 155.32, 162.68, 168.78, 172.89; and MS (Da): [M+H]$^+$ 547.29, [M+Na]$^+$569.27, [M+K]$^+$585.25, [2M+Na]$^+$ 1115.61.

In another aspect, the invention encompasses a process for synthesizing Compound 1. The structure of Compound 1 is determined by structural analysis of both the synthesized compound and the isolated compound from the preparation of mycophenolate mofetil. A mycophenolate mofetil impurity prepared by an independent chemical synthesis is indistinguishable from that isolated from the reaction mixture containing mycophenolate mofetil. By increasing the reaction time of the preparation of mycophenolate mofetil significantly after the reaction is finished, it is possible to receive relatively large amounts of this impurity.

Compound 1 may be synthesized by reacting mycophenolate mofetil with an N-ethylmorpholine derivative.

This process comprises: a) combining mycophenolate mofetil in an aprotic organic solvent with 4-(2-chloroethyl)-morpholine hydrochloride in the presence of a base to obtain a mixture; b) maintaining the mixture for at least 1 day to produce Compound 1, c) extracting Compound 1 with a water-immiscible organic solvent; and d) recovering Compound 1.

The aprotic organic solvent used in step a) may be dichloromethane, tetrahydrofuran, or dimethylformamide, preferably dimethylformamide. The base may be either an organic base (e.g. triethylamine, imidazole) or an inorganic base (e.g. sodium hydride, sodium or potassium carbonate), preferably potassium carbonate. The water-immiscible organic solvent in step c) may be dicloromethane, ethyl acetate, isobutyl acetate or toluene, preferably toluene.

Recovery of Compound 1 may be performed by any method known in the art, such as washing and drying the organic extracts, followed by evaporation of the organic solvent.

In another aspect, the invention encompasses a process for preparing Compound 1 comprising: a) converting N-(2-hydroxyethyl)morpholine to N-(2-mesylethyl)morpholine and b) combining mycophenolate mofetil with the N-(2-mesylethyl)morpholine to form Compound 1.

Preferably, the first reaction, step a), is performed in the presence of an organic base that is a $C_3$-$C_9$ alkyl amine, such as triethylamine, and a solvent, such as toluene, dichloroethane, or preferably, dichloromethane (DCM). More preferably, step a) is performed in the presence of triethylamine ($Et_3N$) and DCM. This reaction may be performed by adding mesylchloride, tosyl chloride (TsCl), or triflic anhydride. Preferably, mesylchloride is added. The reaction mixture may be cooled to about 0° C., while the mesylchloride is added. Preferably, the reaction mixture is stirred overnight and then quenched with water.

The product of the first reaction, N-(2-mesylethyl)morpholine, may be isolated by extraction with ethyl acetate, toluene, or preferably, DCM. Isolation may also include washing, drying, and/or concentrating the N-(2-mesylethyl) morpholine. For example, the N-(2-mesylethyl)morpholine may be washed with brine, dried over $MgSO_4$, and concentrated under reduced pressure.

For the second reaction step, step b), mycophenolate mofetil may be combined with a suitable solvent, preferably DMF, and a base such as sodium hydride, e.g., 60% sodium hydride in mineral oil. Preferably, the sodium hydride is added portionwise over a period of 10 minutes to the mycophenolate mofetil. This second reaction mixture may be stirred at room temperature for about 25 minutes. Then, the N-(2-mesylethyl)morpholine may be added, preferably with stirring at room temperature for about 24 hours. This reaction mixture may be heated to about 25 to about 70° C., preferably about 50° C. For example, the mixture can be heated to 50° C. in an oil bath for about 14 hours. This reaction mixture may also be cooled. For example, the mixture can be allowed to cool to about room temperature.

The second reaction step yields Compound 1, which may be isolated by extraction with a $C_3$-$C_7$ ester or ketone, such as methyl ethyl ketone (MEK) or preferably, ethyl acetate. The extraction may be preceded by dilution with water. The isolation may also include washing, drying, and/or concentrating Compound 1. For example, Compound 1 can be washed with brine, dried, and concentrated under reduced pressure.

Compound 1 may also be purified, such as by column chromatography. For example, the purification can be performed by column chromatography on silica gel with elution with DCM:MeOH (95:5).

In one aspect, the invention encompasses a method for the isolation of Compound 1 from the reaction mixture obtained during the preparation of mycophenolate mofetil. This method comprises: a) providing a solution of mycophenolate mofetil in a suitable solvent; b) washing the mycophenolate mofetil solution with an aqueous acidic solution to obtain a two-phase system; c) separating the organic phase containing mycophenolate mofetil from the aqueous acidic phase; d) adding an aqueous basic solution to the aqueous acidic phase; and e) recovering Compound 1.

The term "suitable solvent" refers to any organic solvent or solvent mixture that is not miscible with water and in which the reaction mass is soluble. Examples of suitable solvents include, but are not limited to, alkyl acetates, chlorinated hydrocarbons such as dichloromethane, chloroform, etc., and aromatic hydrocarbons such as toluene. Preferably, isobutyl acetate is used.

The acid used in the aqueous acid solution for washing may be either a mineral acid or an organic acid. Examples of mineral acid include, but are not limited to, at least one of hydrochloric acid, sulfuric acid, or phosphoric acid. Examples of suitable organic acids include, but are not limited to, at least one of carboxylic acids such as acetic acid, or substituted carboxylic acids such as trifluoroacetic acid, sulfonic acids such as methanesulfonic acid, and substituted sulfonic acids such as trifluoromethanesulfonic acid. Preferably, acetic acid is used. A preferred pH range is about 3 to about 6, more preferably about 4 to about 5.

The base used in the aqueous base solution for washing may be either an inorganic or organic base. Examples of suitable inorganic bases include, but are not limited to, at least one of carbonates, hydroxides, or hydrogen carbonates. A suitable organic base may be, for example, triethylamine. Preferably, sodium bicarbonate is used. A preferred pH range is about 8 to about 11.

Mycophenolate mofetil may be prepared from mycophenolate acid according to any method known in the art, such as the esterification method described in commonly-owned U.S. application Ser. No. 11/115,820 . This method comprises:

reacting a mycophenolic acid of formula:

with a $C_1$ to $C_4$ alcohol or 4-(2-hydroxyethyl)morpholine in the presence of a catalyst, to obtain an ester of mycophenolic acid of formula:

wherein R is $C_1$ to $C_4$ alkyl or a group.

In another aspect, the invention encompasses mycophenolate mofetil having an amount of Compound 1 of about 0.01 to about 0.1% area by HPLC. This mycophenolate mofetil may be prepared by the esterification of mycophenolic acid, according to the process described above.

The amount of Compound 1 can be increased up to 10% (HPLC) in the reaction mixture by changing the reaction conditions to facilitate the isolation of Compound 1. HPLC analysis of reaction mixtures obtained in forced reactions (such as higher temperature and/or longer reaction time) produced results illustrated in Table 1.

TABLE 1

| Starting material | HEM (mol. Equiv) | SnCl$_2$•2H$_2$O (mol %) | Temperature (° C.) | Reaction time (hours) | Compound 1 (HPLC a %) |
|---|---|---|---|---|---|
| MPA | 6 | 10 | 160 | 4 | 0.60 |
| MPA | 6 | 15 | 160 | 4 | 0.33 |
| MPA | 6 | 15 | 140 | 12 | 0.15 |
| MPA | 6 | 3 | 170 | 4 | 2.37 |
| MPA | 3 | 15 | 160 | 4 | 0.85 |
| MPA | 2 | 20 | 165 | 4 | 0.61 |
| MPA | 3 | 15 | 180 | 4 | 4.16 |
| MPA | 3 | 3 | 160 | 4 | 0.70 |
| MPA | 4 | — | 160 | 6 | 0.17 |
| MPA | 6.8 | — | 160 | 107 | 6.8 |
| MMF | 3.8 | — | 160 | 114 | 9.3 |
| MPA-Me* | 6.8 | — | 160 | 107 | 5.9 |

*MPA-Me: mycophenolic acid methyl ester (methyl mycophenolate)

Results from experiments with other catalysts are summarized in Table 2.

TABLE 2

| Starting material | HEM (mol. equiv) | Catalyst (mol %) | Temperature (° C.) | Reaction time (hours) | Compound 1 (HPLC a %) |
|---|---|---|---|---|---|
| MPA | 4 | CSA (3) | 150 | 8 | 0.24 |
| MPA | 6 | PTSA (3) | 190 | 6 | 0.63 |
| MPA | 4 | PTSA (20) | 165 | 4 | 0.78 |
| MPA | 6 | FeCl$_3$ (3) | 190 | 6 | 5.7 |
| MPA | 6 | CaCl$_2$ (1) | 160 | 6 | 1.20 |
| MPA | 4 | K$_2$S$_2$O$_5$ (10) | 160 | 5 | 0.42 |
| MPA | 6 | ZnSO$_4$•7H$_2$O (3) | 165 | 4 | 0.27 |
| MPA | 4 | KAl(SO$_4$)$_2$•12H$_2$O (3) | 165 | 8 | 1.50 |
| MPA | 6 | HCOOH (400) | 165 | 4 | 1.10 |
| MPA | 6 | MgSO$_4$ (3) | 165 | 4 | 0.24 |
| MPA | 4 | KH$_2$PO$_4$ (3) | 165 | 3 | 0.30 |

Compound 1 may be used in a method for analyzing a sample of mycophenolate mofetil by performing chromatography on the sample to obtain data and comparing the data with the chromatography data of Compound 1. The impurity used may or may not be with mycophenolate mofetil, i.e., data may be generated for both the impurity and mycophenolate mofetil simultaneously (as part of the same solution/chromatogram) or separately. One of skill in the art may prepare a solution of mycophenolate mofetil containing Compound 1, subjecting the solution to a high pressure liquid chromatography to obtain a chromatogram and comparing a peak obtained in the chromatogram to a peak resulting from Compound 1. Further, one of skill in the art may prepare a solution of mycophenolate mofetil containing the compound 1, subject the solution to thin layer chromatography to obtain a chromatogram and compare a band or spot obtained in the chromatogram to a peak or band resulting from the degradation product. The impurity may also be used to select desirable batches with high purity at different stages during production and manufacturing.

The present invention also provides a gradient elution HPLC method for quantifying, by area percent, the amounts of all impurities present in a sample of mycophenolate mofetil. The method for determining the purity of mycophenolate mofetil includes the steps of: (a) preparing a sample solution of the mycophenolate mofetil in acetonitrile; (b) injecting the sample solution onto an HPLC column, preferably a C8 column; (c) eluting the sample with a solvent, preferably a mixture of acetonitrile and water; (d) adding a base, such as triethylamine, and adjusting the pH to about 6; and (e) measuring of the amounts of each impurity with a detector (attached to an appropriate recording device).

Preferably, the method for determining the amount of impurities in a mycophenolate mofetil sample comprises the steps of: (a) preparing a sample solution of the mycophenolate mofetil sample in acetonitrile; (b) injecting the sample solution (ca. 10 µL) onto an about 250.0 mm×4.6 mm, 5 µm C8 HPLC column; (c) gradient eluting the sample with a mixture of acetonitrile (about 350 mL) and water (about 650 mL); (d) adding about 2.0 mL of triethylamine and adjusting the pH to about 6 (preferably 5.9) with diluted phosphoric acid (A Eluent) and a B Eluent with a buffer: acetonitrile ratio of about 15:85; and (e) measuring of the amounts of each impurity at 250 nm wavelength with a UV detector (having an appropriate recording device).

The buffer may be prepared by mixing about 1 L water with about 3.0 mL of triethylamine and adjusted to pH 5.9 with diluted phosphoric acid.

The HPLC profile for determining the purity of is mycophenolate mofetil exemplified in Table 3.

TABLE 3

| HPLC Gradient | | | |
|---|---|---|---|
| Flow rate [mL/min] | Time (min) | A Eluent (V/V %) | B Eluent (V/V %) |
| 1.5 | 0 | 100 | 0 |
| 1.5 | 15 | 100 | 0 |
| 1.5 | 37 | 28 | 72 |
| 1.5 | 37.1 | 100 | 0 |
| 1.5 | 40 | 100 | 0 |

In the method described above, mycophenolate mofetil has a retention time of about 20.8 minutes.

Another aspect of the invention encompasses a method for determining the purity of mycophenolate mofetil comprising using Compound 1 as a reference marker.

Pharmaceutical compositions may be prepared as medicaments to be administered orally, parenterally, rectally, transdermally, bucally, or nasally. Suitable forms for oral administration include tablets, compressed or coated pills, dragees, sachets, hard or gelatin capsules, sub-lingual tablets, syrups and suspensions. Suitable forms of parenteral administration include an aqueous or non-aqueous solution or emulsion, while for rectal administration suitable forms for administration include suppositories with hydrophilic or hydrophobic vehicle. For topical administration the invention provides suitable transdermal delivery systems known in the art, and for nasal delivery there are provided suitable aerosol delivery systems known in the art.

Pharmaceutical compositions of the present invention contain mycophenolate mofetil comprising Compound 1 in an amount of about 0.01 to about 0.1% area by HPLC. In addition to the active ingredient(s), the pharmaceutical compositions of the present invention may contain one or more excipients or adjuvants. Selection of excipients and the amounts to use may be readily determined by the formulation scientist based upon experience and consideration of standard procedures and reference works in the field.

Diluents increase the bulk of a solid pharmaceutical composition and may make a pharmaceutical dosage form containing the composition easier for the patient and care giver to handle. Diluents for solid compositions include, for example, microcrystalline cellulose (e.g. Avicel®), microfine cellulose, lactose, starch, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol, and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®), and starch.

Glidants can be added to improve the flowability of a non-compacted solid composition and to improve the accuracy of dosing. Excipients that may function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

In liquid pharmaceutical compositions of the present invention, the active ingredient and any other solid excipients are suspended in a liquid carrier such as water, vegetable oil, alcohol, polyethylene glycol, propylene glycol, or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present invention may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as sorbitol, saccharin, sodium saccharin, sucrose, aspartame, fructose, mannitol, and invert sugar may be added to improve the taste.

Preservatives and chelating agents such as alcohol, sodium benzoate, butylated hydroxy toluene, butylated hydroxyanisole, and ethylenediamine tetraacetic acid may be added at levels safe for ingestion to improve storage stability.

According to the present invention, a liquid composition may also contain a buffer such as gluconic acid, lactic acid, citric acid or acetic acid, sodium gluconate, sodium lactate, sodium citrate, or sodium acetate.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable administration in any given case will depend on the nature and severity of the condition being treated, the most preferred route of the present invention is oral. The dosages may be conveniently presented in unit dosage form and prepared by any of the methods well-known in the pharmaceutical arts.

Dosage forms include solid dosage forms like tablets, powders, capsules, suppositories, sachets, troches, and lozenges, as well as liquid syrups, suspensions, and elixirs.

The dosage form of the present invention may be a capsule containing the composition, preferably a powdered or granulated solid composition of the invention, within either a hard or soft shell. The shell may be made from gelatin and optionally contain a plasticizer such as glycerin and sorbitol, and an opacifying agent or colorant.

The active ingredient and excipients may be formulated into compositions and dosage forms according to methods known in the art.

A composition for tableting or capsule filling may be prepared by wet granulation. In wet granulation, some or all of the active ingredients and excipients in powder form are blended and then further mixed in the presence of a liquid, typically water, that causes the powders to clump into granules. The granulate is screened and/or milled, dried, and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present invention may comprise any of the aforementioned blends and granulates that were described with reference to tableting, however, they are not subjected to a final tableting step.

EXAMPLES

Example 1

Preparation of N-(2-mesylethyl)morpholine

A 150 ml one-necked round bottomed flask equipped with magnetic bar and equipped with $CaCl_2$ tube on its top, was charged with 5.2 g N-(2-hydroxyethyl)morpholine, 25 ml DCM, and 5.5 ml triethylamine. The mixture was stirred and cooled in an ice-water bath while 3.1 ml of mesylchloride was added over a period of 5 min. The reaction mixture was stirred overnight and then quenched in 20 ml water. The aqueous layer was extracted with two 25 ml DCM portions, and the combined organic extracts were washed with 20 ml of brine, dried over $MgSO_4$, and concentrated under reduced pressure to give 4.1 g of the crude mesylate which is pure by TLC.

Example 2

Preparation of Compound 1

A 150 ml two-necked round bottomed flask with a magnetic stirrer and a nitrogen gas inlet, was charged with 6.21 g mycophenolate mofetil (14.3 mmol) and 20 ml anhydrous DMF. To the stirred solution was added portion wise 570 mg sodium hydride (60% in mineral oil) over a period of 10 min, and the resulting mixture was stirred for 25 min at room temperature. To the reaction mixture was added mesyl derivative, 2.92 g (14 mmol) in 4 ml DMF. The reaction mixture was heated in a 50° C. oil bath for 14 hrs, and then allowed to cool to room temperature, diluted with 50 ml water, and extracted with three 20 ml portions of ethyl acetate. The combined organic extracts were washed with brine (20 ml), dried, and concentrated under reduced pressure to give 7 g (89%) pale viscous yellow liquid as a pure product (by TLC analysis). Further purification can be conducted by column chromatography on silica gel and elution with DCM/MeOH (95:5).

Example 3

Preparation of Compound 1

Combined aqueous acetic washings (5 l) derived from the production of crude MMF were neutralized with solid sodium bicarbonate. Isobutyl acetate (1 l) and charcoal (10 g) were added, filtered, and the phases were separated. The organic phase was evaporated to 300 ml. Water (300 ml) was added, and the pH was adjusted to 4-4.5 using acetic acid. After separation of phases, the aqueous phase was neutralized with solid sodium bicarbonate and extracted with isobutyl acetate (200 ml). The organic phase was dried on sodium sulfate and evaporated to dryness. The purity of the residue (0.81 g brownish oil) was 77 a % of Compound 1.

The residue was chromatographed on a column of silica gel (eluent: acetone) to produce a syrupy product, Compound 1 (560 mg, purity: 95 a %).

Example 4

Preparation of Compound 1

MMF (26.04 g, 60 mmol) was stirred in DMF (40 ml). Potassium carbonate (33.17 g, 4 equiv) and 4-(2-chloroethyl)morpholine hydrochloride (14.53 g, 1.3 equiv) were added. The mixture was stirred at room temperature for 3 days, diluted with water (400 ml), and extracted with toluene (2×300 ml). The combined organic phase were washed with water (2×300 ml), dried on sodium sulfate, and evaporated to dryness. The residue was Compound 1 as a yellowish oil (32.5 g, purity: 95 a %).

Example 5

Preparation of pure mycophenolate mofetil

A mixture of mycophenolic acid (192 g, 0.6 mol) and 4-(2-hydroxyethyl)-morpholine (440 ml, 6 molar equivalents) was stirred at 150-155° C. for 4 hours in the presence of tin(II) chloride dihydrate (20.4 g, 0.15 molar equivalents) under nitrogen atmosphere. After the completion of the reaction, the reaction mixture was allowed to cool to room temperature. The obtained dark liquid was poured into isobutyl acetate (4.0 l). The solution was extracted with 2% of aqueous sodium bicarbonate solution (1.2 l, then 2×0.4 l). After the first addition of sodium bicarbonate solution the formed two-phase system was treated with charcoal (40 g) and filtrated (an emulsion was filtered off). The solution was extracted with water (1 l). -After phase separation the organic phase was washed with water (1 l) and evaporated to dryness at 40-50° C. under vacuum. To the solid material acetone (400 ml) and isopropanol (3.8 l) were added and the mixture was warmed to 40-45° C. (the material was dissolved). The solution was cooled to −5° C. during 6 hours and it was stirred at this temperature for 10-12 hours. After filtration, the crystals were washed with 2:19 acetone/isopropanol mixture (420 ml). The crude compound was dried in vacuum at 60° C. The yield was 169-195 g (65-75%). HPLC impurity profile: MPA=0.1%. Assay: 99.85%.

Having thus described the invention with reference to particular preferred embodiments and illustrated it with Examples, those in the art can appreciate modifications to the invention as described and illustrated that do not depart from the spirit and scope of the invention as disclosed in the specification. The Examples are set forth to aid in understanding the invention but are not intended to, and should not be construed to, limit its scope in any way. The examples do not include detailed descriptions of conventional methods. All references mentioned herein are incorporated in their entirety.

What is claimed is:

1. A Compound having the formula:

Compound 1

2. The compound of claim 1, characterized by $^1$H NMR (300 MHz, CDCl$_3$) δ (ppm): 1.73, 2.10, 2.21, 2.32, 2.39, 2.49, 2.74, 3.38, 3.60, 3.64, 3.69, 4.08, 4.26, 5.05 and 5.09.

3. The compound of claim 1, characterized by $^{13}$C NMR (75 MHz, CDCl$_3$) δ (ppm): 11.35, 16.15, 23.33, 32.78, 34.27, 53.60, 53.70, 56.88, 58.38, 60.75, 61.21, 66.66, 66.68, 68.11, 71.91, 112.41, 119.89, 123.57, 128.90, 133.51, 146.55, 155.32, 162.68, 168.78 and 172.89.

4. The compound of claim 1, characterized by MS (Da): [M+H]$^+$547.29, [M+Na]$^+$569.27, [M+K]$^+$585.25, [2M+Na]$^+$1115.61.

5. The compound of claim 1, wherein the compound is isolated.

6. A process for preparing the compound of claim 1 comprising:
   a) combining mycophenolate mofetil in an aprotic organic solvent with an N-ethylmorpholine derivative in presence of a base to obtain a mixture;
   b) maintaining the mixture for at least about 24 hours to produce Compound 1;
   c) extracting Compound 1 with a water-immiscible organic solvent; and
   d) recovering Compound 1.

7. The process of claim 6, wherein the N-ethylmorpholine derivative is 4-(2-chloroethyl)-morpholine hydrochloride.

8. The process of claim 6, wherein the aprotic organic solvent in step a) is dichloromethane, tetrahydrofuran, or dimethylformamide.

9. The process of claim 8, wherein the aprotic organic solvent in step a) is dimethylformamide.

10. The process of claim 6, wherein the base in step b) is either organic or inorganic.

11. The process of claim 10, wherein the base is potassium carbonate.

12. The process of claim 6, wherein the water-immiscible organic solvent in step c) is dicloromethane, ethyl acetate, isobutyl acetate or toluene.

13. The process of claim 12, wherein the a water-immiscible organic solvent in step c) is toluene.

14. The process of claim 6, wherein the morpholine agent is N-(2-mesylethyl)morpholine.

15. The process of claim 14, wherein base in step b) is sodium hydride.

16. The process of claim 14, further comprising heating the mixture obtained in step a) to a temperature of about 25 to about 70° C., followed by cooling of the mixture to room temperature.

17. The process of claim 16, wherein said mixture is heated to a temperature of about 50° C.

18. The process of claim 14, wherein the water-immiscible organic solvent in step c) is with a C$_3$-C$_7$ ester or ketone.

19. The process of claim 18, wherein said water-immiscible organic solvent is ethyl acetate.

20. The process of claim 14, wherein N-(2-mesylethyl)morpholine is obtained by the process comprising:
   a) reacting, at a temperature of about 0° C., N-(2-hydroxyethyl)morpholine in a solvent and an organic base with mesylchloride, tosyl chloride (TsCl), or triflic anhydride; and
   b) extracting the product obtained in step a) with ethyl acetate, toluene, or dichloromethane.

* * * * *

UNITED STATES PATENT AND TRADEMARK OFFICE
CERTIFICATE OF CORRECTION

| | |
|---|---|
| PATENT NO. | : 7,358,247 B2 |
| APPLICATION NO. | : 11/115593 |
| DATED | : April 15, 2008 |
| INVENTOR(S) | : Molnar et al. |

It is certified that error appears in the above-identified patent and that said Letters Patent is hereby corrected as shown below:

Column 7
Line 28, change "25" to --25°C--

Column 10
Line 9, change "(ca. 10 µL)" to --(about 10µL)--

Column 13
Line 41, change "150 ml" to --150 mL--
Line 43, change "25 ml" to --25 mL--
Line 44, change "5.5 ml" to --5.5 mL--
Line 45, change "3.1 ml" to --3.1 mL--
Line 47, change "quenched" to --diluted--
Line 47, change "20 ml" to --20 mL--
Line 48, change "25 ml" to --25 mL--
Line 49, change "20 ml" to --20 mL--
Line 51, change "is pure" to --was pure--
Line 58, change "150 ml" to --150 mL--
Line 60, change "20 ml" to --20 mL--
Line 65, change "4 ml" to --4 mL--
Line 67, change "50 ml" to --50 mL--

Column 14
Line 1, change "20 ml" to --20 mL--
Line 3, change "20 ml" to --20 mL--
Line 13, change "(5 1)" to --(5 L)--
Line 15, change "(1 1)" to --(1 L)--
Line 17, change "300 ml. Water (300 ml) was" to --300 mL. Water (300 mL) was--
Line 21, change "200 ml" to --200 mL--
Line 26, change "95 a %" to --95%--
Line 33, change "60 mmol" to --60 mol--
Line 33, change "40 ml" to --40 mL--
Line 37, change "400 ml" to --400 mL--
Line 38, change "2x300 ml" to --2x300 mL--
Line 39, change "2x300 ml" to --2x300 mL--
Line 41, change "95 a %" to --95%--
Line 48, change "4-(2-hydroxyethyl)-morpholine" to --4-(2-hydroxyethyl)morpholine--
Line 48, change "440 ml" to --440 mL--
Line 51, change "After the" to --Upon--

UNITED STATES PATENT AND TRADEMARK OFFICE
CERTIFICATE OF CORRECTION

PATENT NO. : 7,358,247 B2
APPLICATION NO. : 11/115593
DATED : April 15, 2008
INVENTOR(S) : Molnar et al.

It is certified that error appears in the above-identified patent and that said Letters Patent is hereby corrected as shown below:

Line 53, change "The obtained dark liquid" to --The dark liquid obtained--
Line 54, change "(4.0 l)" to --(4.0 L)--
Line 55, change "(1.2 l, then 2x0.4 l)" to --(1.2 L, then 2x0.4 L)--
Line 59, change "(1 l). -After" to --(1 L). After--
Line 60, change "(1 l)" to --(1 L)--
Line 62, change "(400 ml) and isopropanol (3.8 l)" to --(400 mL) and isopropanol (3.8 L)--
Line 64, change "to -5° C. during 6 hours" to --to -5° C over a period of 6 hours--
Lines 65-66, change "After filtration" to --Once filtered--
Line 67, change "(420 ml)" to --420 mL--

<u>Column 16</u>
Line 7, change "4-(2-chloroethyl)-morpholine" to --4-(2-chloroethyl)morpholine--

Signed and Sealed this

Sixteenth Day of June, 2009

JOHN DOLL
*Acting Director of the United States Patent and Trademark Office*